United States Patent
Mehra et al.

(10) Patent No.: US 10,748,664 B2
(45) Date of Patent: Aug. 18, 2020

(54) ROLE BASED COMMUNICATION

(71) Applicant: CERNER INNOVATION, INC., Kansas City, KS (US)

(72) Inventors: Rajneesh Mehra, Overland Park, KS (US); Chris Cline, Smithville, MO (US); Kris Kline, Overland Park, KS (US); Andrew Dittrich, Overland Park, KS (US); Jonathan M. Castaneda, Overland Park, KS (US); Chad G. Hays, Overland Park, KS (US); Aravind R. Mereddi, Overland Park, KS (US); Steven E. Harlow, Lee's Summit, MO (US); Jill R. Clum, Lenexa, KS (US)

(73) Assignee: CERNER INNOVATION, INC., Kansas City, KS (US)

( * ) Notice: Subject to any disclaimer, the term of this patent is extended or adjusted under 35 U.S.C. 154(b) by 991 days.

(21) Appl. No.: 14/725,017

(22) Filed: May 29, 2015

(65) Prior Publication Data
US 2016/0125156 A1    May 5, 2016

Related U.S. Application Data

(60) Provisional application No. 62/073,430, filed on Oct. 31, 2014.

(51) Int. Cl.
| | |
|---|---|
| *G16H 80/00* | (2018.01) |
| *H04W 4/14* | (2009.01) |
| *G16H 40/20* | (2018.01) |
| *H04L 12/58* | (2006.01) |

(52) U.S. Cl.
CPC ............ *G16H 80/00* (2018.01); *G16H 40/20* (2018.01); *H04L 51/14* (2013.01); *H04W 4/14* (2013.01)

(58) Field of Classification Search
None
See application file for complete search history.

(56) References Cited

U.S. PATENT DOCUMENTS

| | | | | |
|---|---|---|---|---|
| 2006/0161457 | A1* | 7/2006 | Rapaport | G06Q 10/10 705/2 |
| 2007/0112602 | A1* | 5/2007 | Bellon | G06F 19/3462 705/3 |
| 2010/0305972 | A1* | 12/2010 | McLaren | G06Q 50/22 705/3 |
| 2010/0305973 | A1* | 12/2010 | McLaren | G16H 40/63 705/3 |

(Continued)

*Primary Examiner* — Michael Tomaszewski
(74) *Attorney, Agent, or Firm* — Shook, Hardy & Bacon, L.L.P.

(57) ABSTRACT

The present invention relates to methods, systems, and computer-readable media for routing healthcare information based on a role associated with a user. Information may not always need to go to a specific person but, rather, may need to be communicated to a role. A user may be associated with a given role based on manually claiming the role, being assigned to a role, or being automatically scheduled into a role. Additionally, information may be communicated using user contact preferences specifying the modality by which the user is to be contacted under various circumstances. Further, the information may be re-directed if a rejection (or lack of response) is received by an initial recipient.

20 Claims, 8 Drawing Sheets

(56) References Cited

U.S. PATENT DOCUMENTS

2011/0202371 A1\* 8/2011 Darguesse ............. G06Q 50/24
 705/3
2013/0006664 A1\* 1/2013 Chaliparambil ....... G06Q 50/22
 705/3

\* cited by examiner

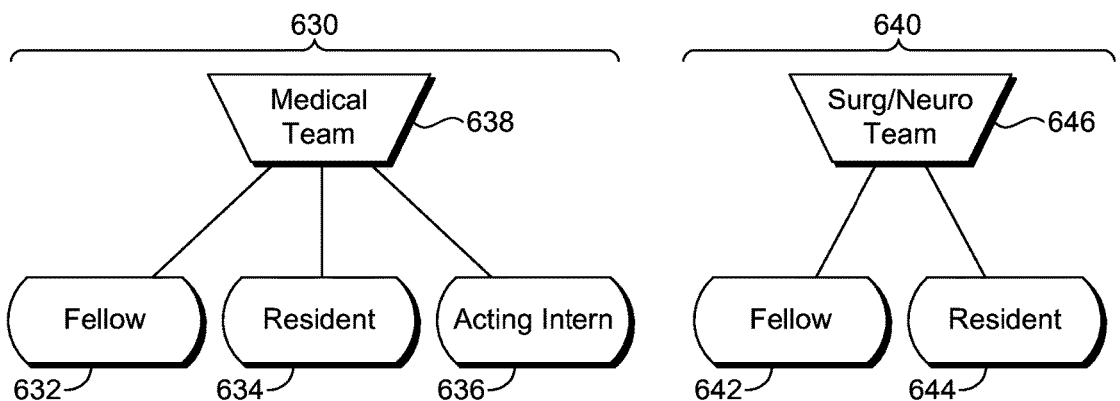
FIG. 6C
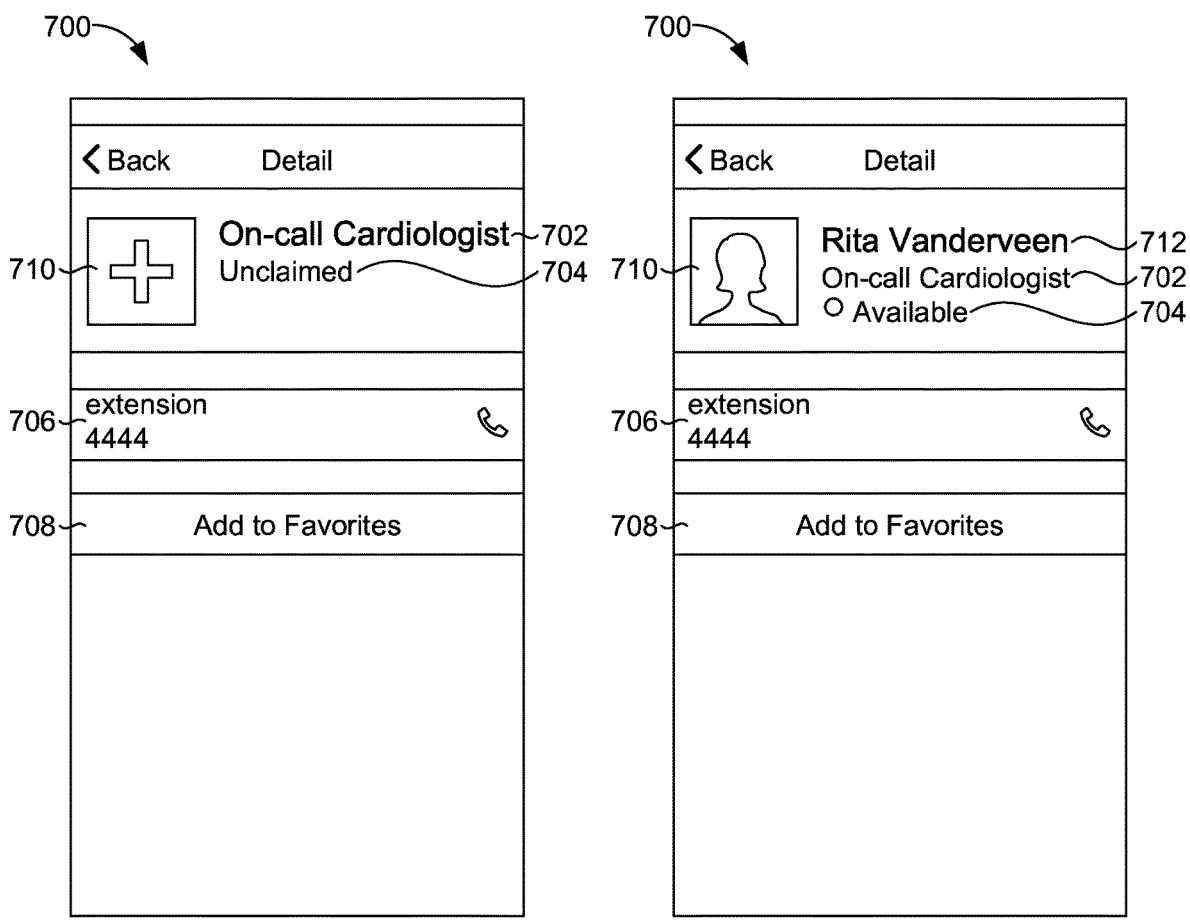
FIG. 7A
FIG. 7B

ROLE BASED COMMUNICATION

CROSS REFERENCE TO RELATED APPLICATIONS

This application claims priority from U.S. Provisional Application No. 62/073,430, filed Oct. 31, 2014, entitled "Intelligent Routing," the entire contents of which are herein incorporated by reference.

BACKGROUND

The nature of the healthcare industry involves constant communication of information. Health care members need to be informed and updated on a variety of issues including patient status, emergency situations, alarms, test results, etc. There are numerous ways to communicate this information and many different people to which the information is communicated. Determining to whom to communicate the information or how to communicate the information may be a time consuming process. Information does not necessarily need to go to an individual but rather, in some situations, may be communicated to a specific role or group. Communicating users then have to look up who is in a particular role, how to contact the person currently in the role, etc., and this leads to inefficient communication, unproductive workflows, and wasted time between when the information is received and when it is acted on by the receiving party.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

In brief and at a high level, this disclosure describes, among other things, methods, systems, and computer-readable media for routing information based on role. As previously mentioned, information may not always need to go to a specific person but, rather, may need to be communicated to a role. A user may be associated with a given role based on manually claiming the role, being assigned to a role, or being automatically scheduled into a role. For instance, an alert that a patient is entering the Emergency Department with a heart attack should be communicated to an on-call cardiologist, rather than specifically to Dr. X who may be a cardiologist but is not necessarily on call at the time of the emergency. Additionally, information may be communicated using user contact preferences (e.g., Alarm type A is communicated to a mobile device but Alarm type B is communicated to an electronic mail account). Further, the information may be re-directed if a rejection (or lack of response) is received by an initial recipient. The intelligent role-based routing may also be used in combination with proximity-based notifications, as described in detail below.

In one embodiment, computer-storage media having computer-executable instructions embodied thereon is executed to perform a method of communicating information to a user based on the user's role. An input to contact a role is received, wherein a role is a position held by a set of user satisfying one or more criteria. Information to communicate to the role is received. One or more users associated with the role are identified. The information is communicated to the one or more users.

In another embodiment, a computerized method is carried out by at least one server having at least one processor to route communications to a user based on the user's role. A user is associated with a role, wherein the role is a position held by one or more users satisfying one or more criteria and wherein the one or more criteria are defined by a job title, hospital service, or location. The user's contact preferences are linked with the role. A communication directed to the role associated with the user is received. The communication to the user is routed according to the user's contact preferences.

In another embodiment, a computer-implemented system is designed to communicate information to a user based on their role. A directory includes a data store of user names, contact information, and roles. A routing service determines a path which a communication takes to reach a user. A communication delivery service sends and receives communications. A role association service associates users with roles.

BRIEF DESCRIPTION OF THE DRAWINGS

Embodiments are described in detail below with reference to the attached drawings figures, wherein:

FIG. 6C is an exemplary chart illustrating various roles associated with teams.

FIG. 7A depicts an exemplary graphical user interface for claiming a role in accordance with an embodiment of the present invention.

FIG. 7B depicts the exemplary graphical user interface of 7A after a user has claimed a role in accordance with an embodiment of the present invention.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention are directed to methods, systems, and computer-readable media for intelligently routing information in a healthcare environment. Information, as used herein, refers to any content that is communicated. Examples include test results, patient statuses, patient alerts, emergency alerts, medical device alerts, coding situations, and the like. In embodiments, secured text messages, emails, and phone calls may also be included in the routed information.

As previously mentioned, information may not always need to go to a specific person but rather, may need to be communicated to a role. A role, as used herein, refers generally to a position held by a set of users satisfying one or more criteria, where a set of users may be one person or a group of people. A user may be associated with a given role based on manually claiming the role, being assigned to a role, or being automatically scheduled into a role. For instance, an alert that a patient is entering the Emergency Department with a heart attack should be communicated to an on-call cardiologist, rather than specifically to Dr. X who may be a cardiologist but is not necessarily on call at the time of the emergency. Additionally, information may be communicated using user contact preferences (e.g., Alarm type A is communicated to a mobile device but Alarm type B is communicated to an electronic mail account). Further, the information may be re-directed if a rejection (or lack of response) is received by an initial recipient. The intelligent role-based routing may also be used in combination with proximity-based notifications, as described in detail below.

Figure 1:
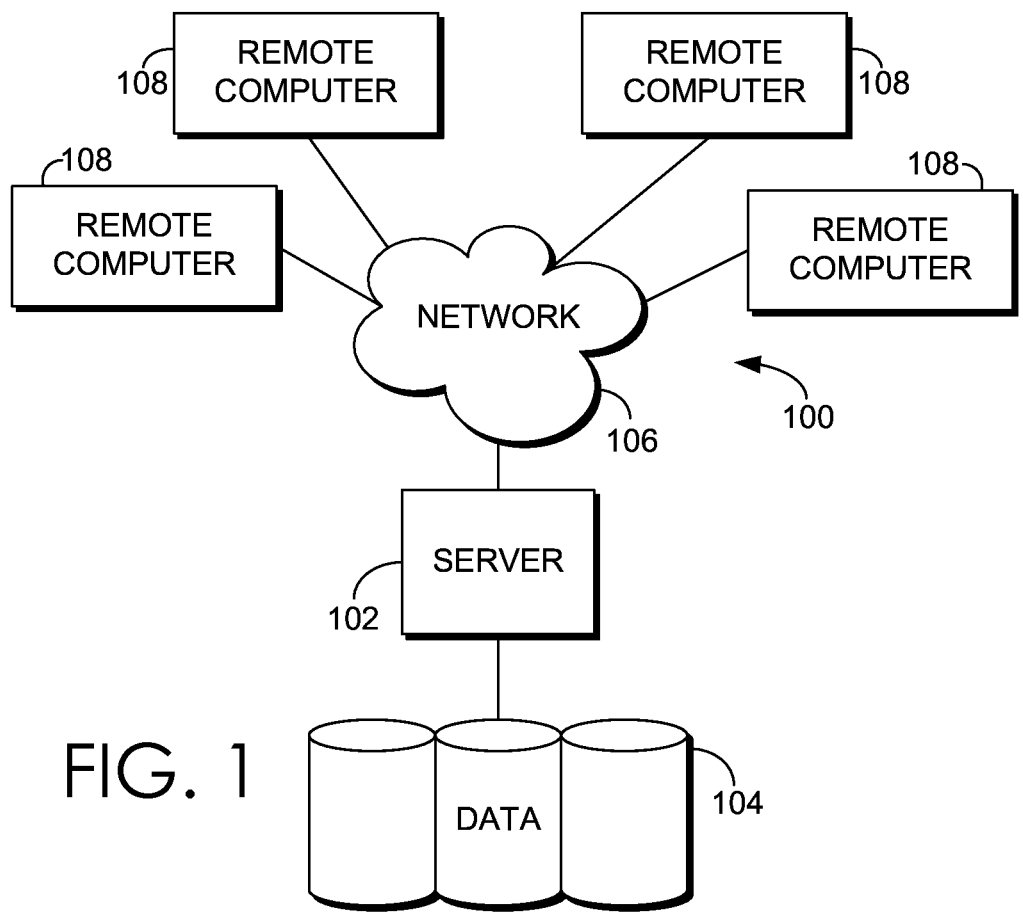
FIG. 1 is a block diagram of an exemplary computing system suitable to implement embodiments of the present invention.

An exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention might be operational with numerous other purpose computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of non-transitory computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a microphone (e.g., voice inputs), a touch screen, a pointing device (commonly referred to as a mouse), a trackball, or a touch pad. Other input devices comprise satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
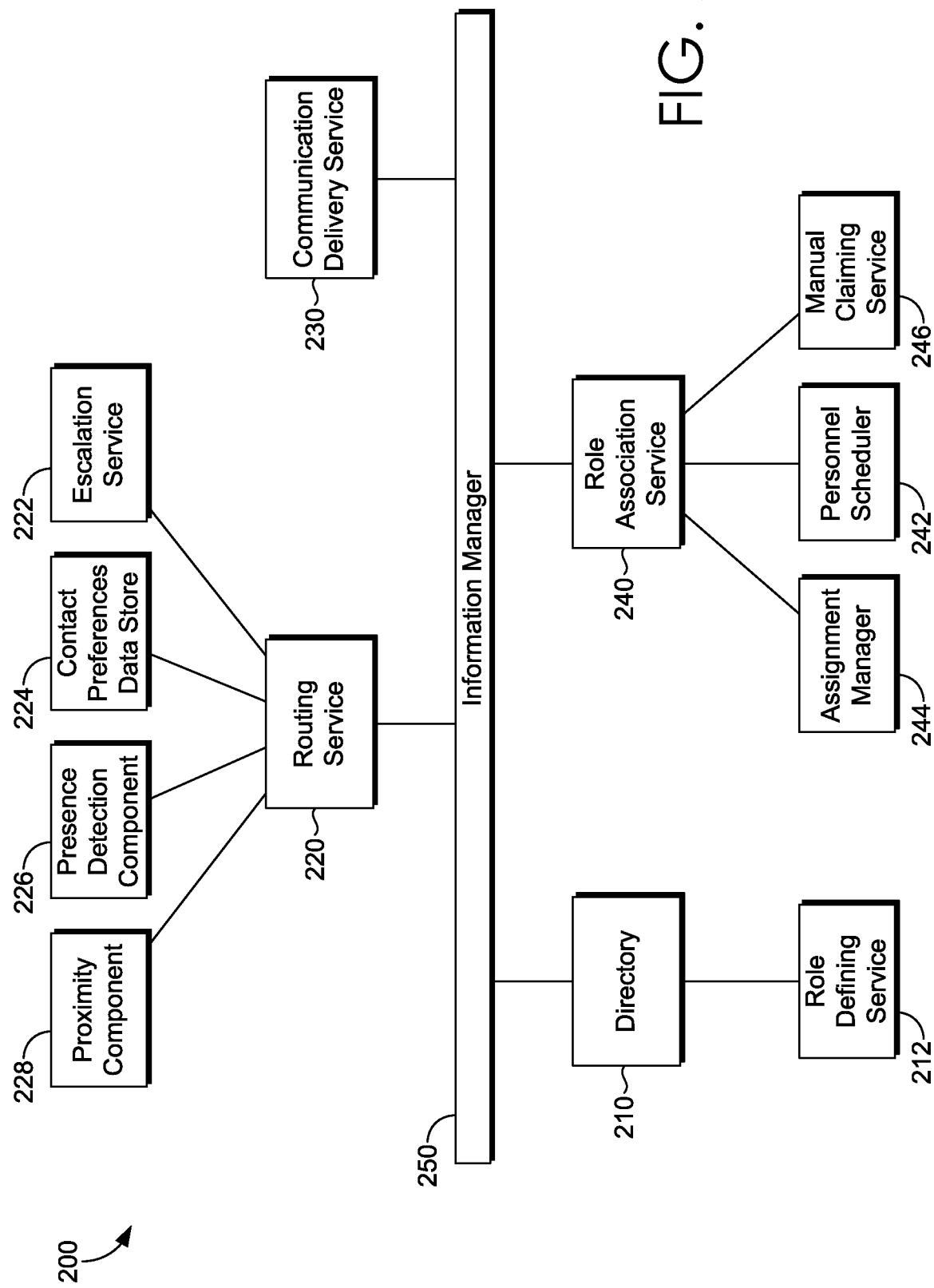
FIG. 2 is a block diagram of an exemplary computing system suitable for managing the communication of information to users based on roles.

Turning now to FIG. 2, an exemplary computing system 200 is depicted. The computing system 200 is merely an example of one suitable computing system and is not intended to suggest any limitation as to the scope of use or functionality of embodiments of the present invention. Neither should the computing system 200 be interpreted as having any dependency or requirement related to any single module/component or combination of modules/components illustrated therein.

The computing system 200 includes a directory 210, a routing service 220, a communication delivery service 230, and a role association service 240 all in communication with one another via an information manager 250. The computing system 200 may also include one or more end-user computing devices to access the system.

The end-user computing device may include a display screen. The display screen may be configured to display information to the user of the end-user computing device, for instance, information relevant to communications initiated by and/or received by the end-user computing device, information related to role claiming activities, information related to workflow behavior/actions, and the like. Embodiments are not intended to be limited to visual display but rather may also include audio presentation, combined audio/visual presentation, and the like. The end-user computing device may be any type of display device suitable for presenting a graphical user interface. Such computing devices may include, without limitation, a computer, such as, for example, any of the remote computers 108 described above with reference to FIG. 1. Other types of display devices may include tablet PCs, PDAs, mobile phones, smart phones, as well as conventional display devices such as televisions. Interaction with the graphical user interface may be via a touch pad, a microphone, a pointing device, and/or gestures.

In some embodiments, one or more of the illustrated components/modules may be implemented as stand-alone applications. In other embodiments, one or more of the illustrated components/modules may be integrated directly into the operating system of the routing service and/or the end-user computing device. The components/modules described are exemplary in nature and in number and should not be construed as limiting. Any number of components/modules may be employed to achieve the desired functionality within the scope of embodiments hereof. Further, components/modules may be located on any number of servers. By way of example only, the routing service might reside on a server, a cluster of servers, or a computing device remote from one or more of the remaining components.

As shown in FIG. 2, the directory 210 is in communication with both the information manager 250 and a role defining service 212. The directory 210 comprises a data store of user names, contact information, and roles. User names correspond with individual clinicians within the healthcare system as well as any other users desired to be included within the directory 210. Contact information may correspond with individual users or particular roles or groups. Contact information may include phone numbers, phone extensions within a facility, fax numbers, pager numbers, instant messaging account information, e-mail addresses, and the like. The role defining service 212 links user names and contact information with roles.

Figure 3:
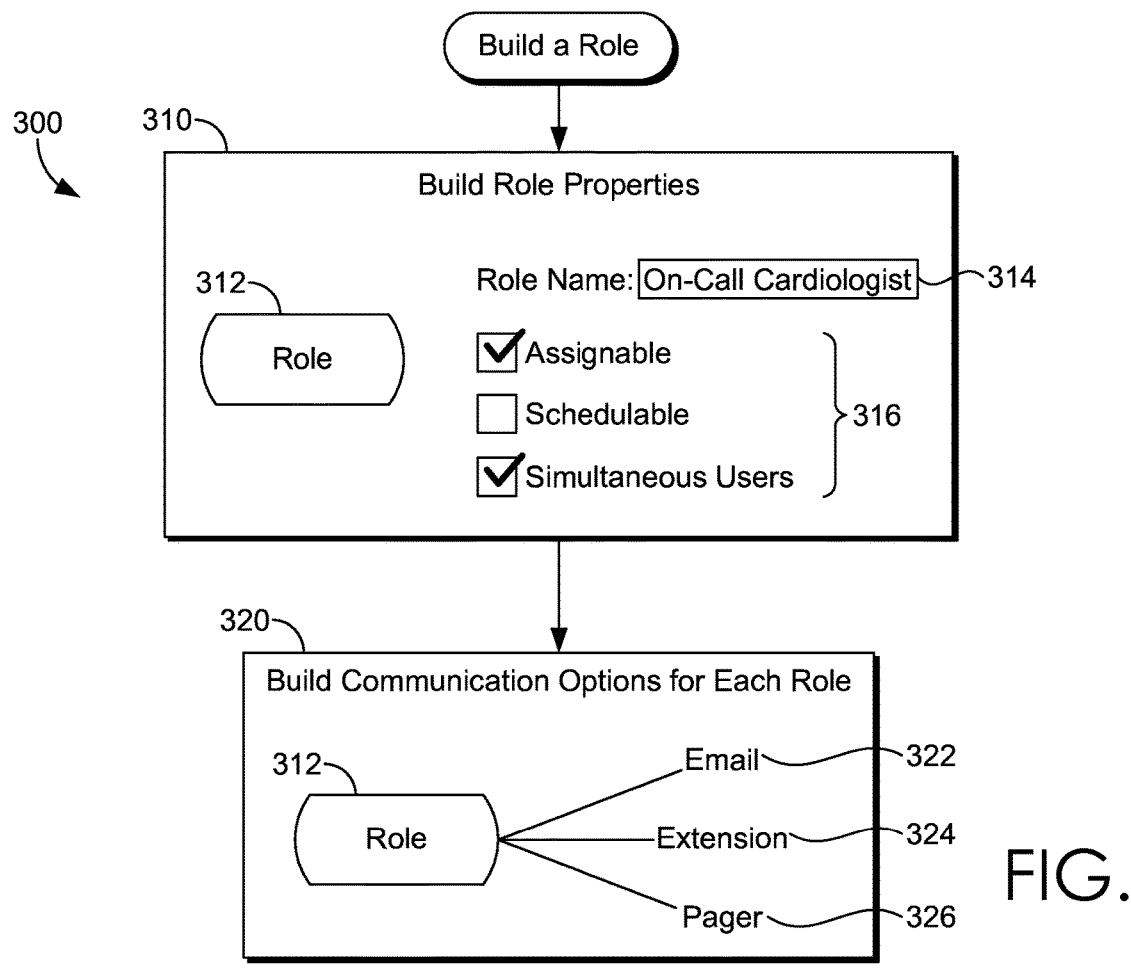
FIG. 3 depicts a flow diagram that illustrates an exemplary method of building a role.

Before being stored in the directory, a new role must be built. FIG. 3 depicts a flow diagram illustrating an exemplary method 300 of building a role. In step 310, role properties are built. The role 312 is given a name 314, for example, "On-Call Cardiologist." Properties 316 are selected for the role, such as selecting whether the role is assignable, schedulable, or allows simultaneous users. Then, in step 320, communication options are built for the role 312. For example, the role 312 may be associated with a particular email address 322, extension number 324, and/or pager number 326.

Figure 4:
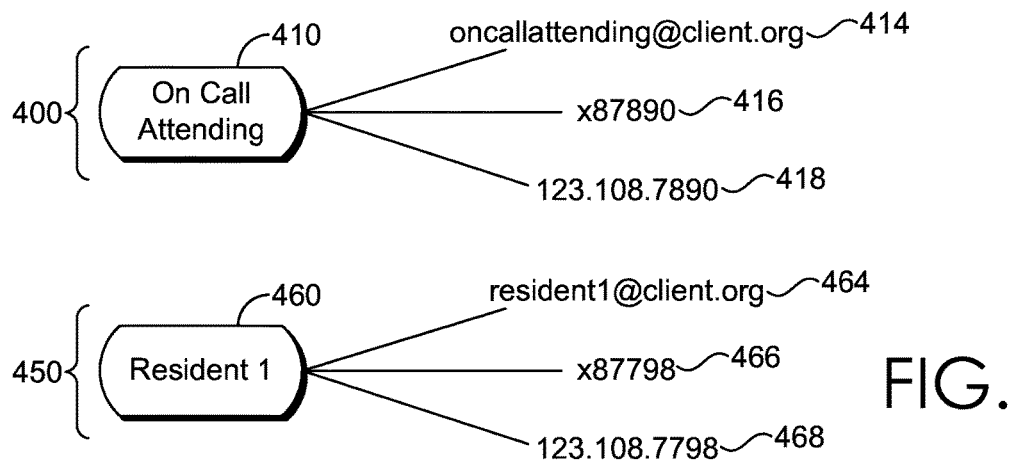
FIG. 4 illustrates examples of roles associated with communication options in accordance with an embodiment of the present invention.

FIG. 4 illustrates examples, 400 and 450, of roles associated with communication options. In example 400, the role 410 is named "On Call Attending" and is associated with the email address 414 "oncallattending@client.org," the extension number 416 "x87890," and the pager number 418 "123.108.7890." In example 450, the role 460 is named "Resident 1" and is associated with the email address 464 "resident1@client.org," the extension number 466 "x87798," and the pager number 468 "123.108.7798." If a first user dials extension x87890, it will contact a second user associated with the role of "On Call Attending." Similarly, if a first user emails resident1@client.org, it will contact a second user associated with the role of "Resident 1." Therefore, the first user does not need to know the name of the user who is associated with the given role at that time.

Figure 5:
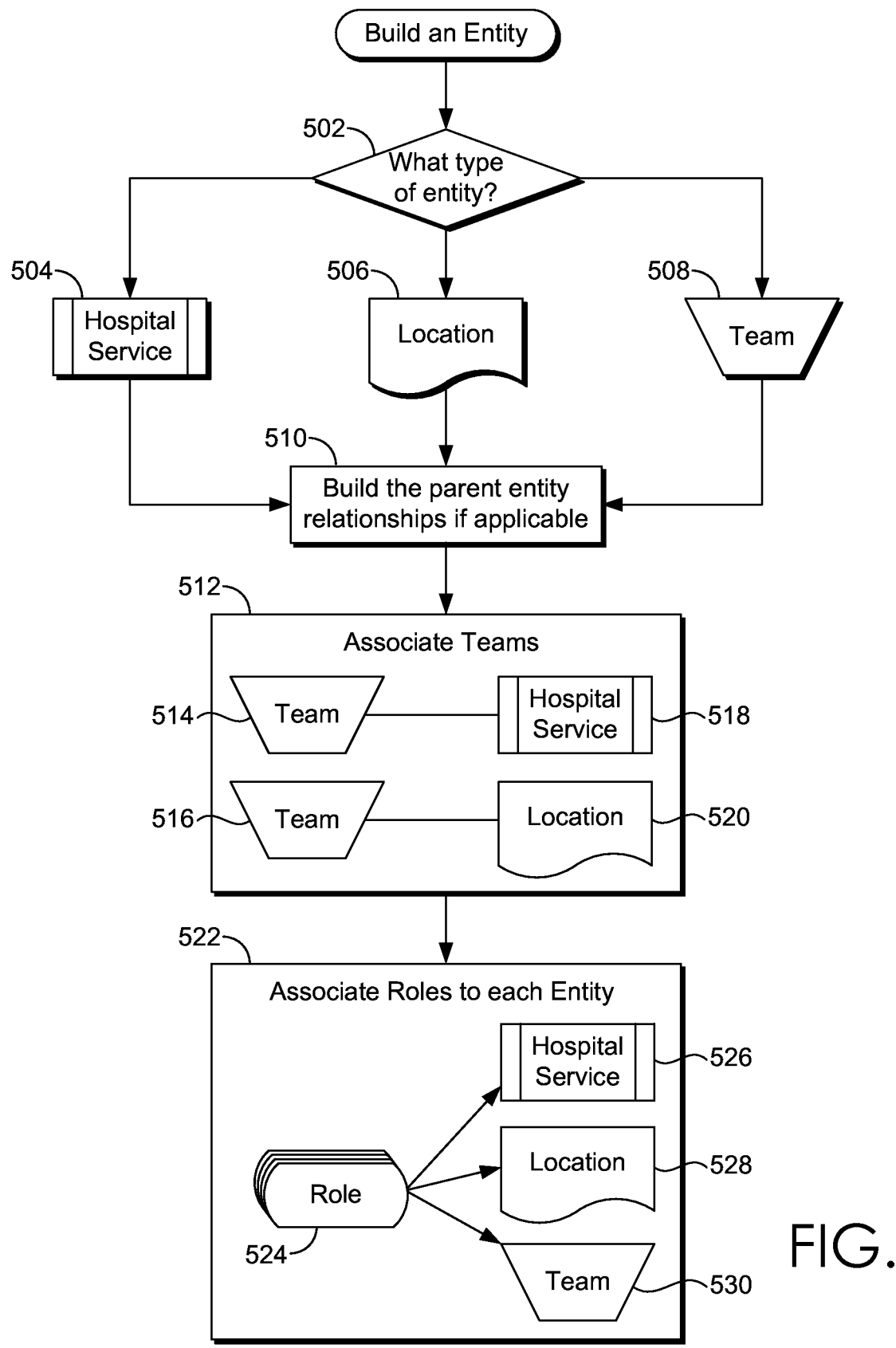
FIG. 5 depicts a flow diagram that illustrates an exemplary method of building an entity.

The data store of directory 210 also stores relationships between roles based on associations with entities. FIG. 5 depicts a flow diagram illustrating an exemplary method 500 of building an entity. In step 502, a type of entity is chosen. The entity may be a hospital service 504, a location 506, or a team 508. At 510, parent entity relationships are built, if applicable. In step 512, relationships are formed by associating a team 514 with a hospital service 518 or a team 516 with a location 520. Then, in step 522, roles 524 are associated with each entity. Roles may be associated with one or more of a hospital service 526, a location 528, or a team 530 at one time.

Figure 6A:
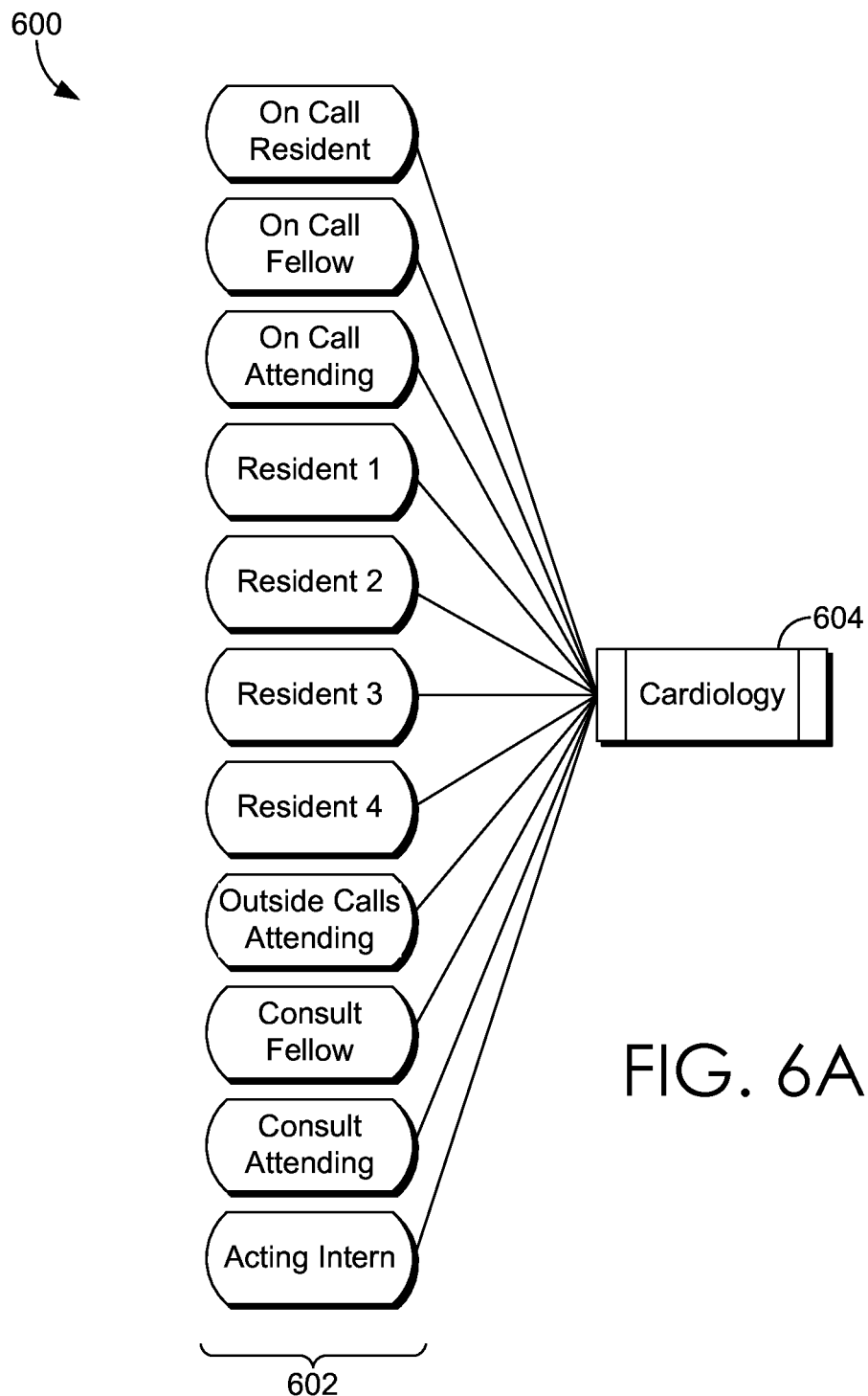
FIG. 6A is an exemplary chart illustrating various roles associated with a hospital service.
Figure 6B:
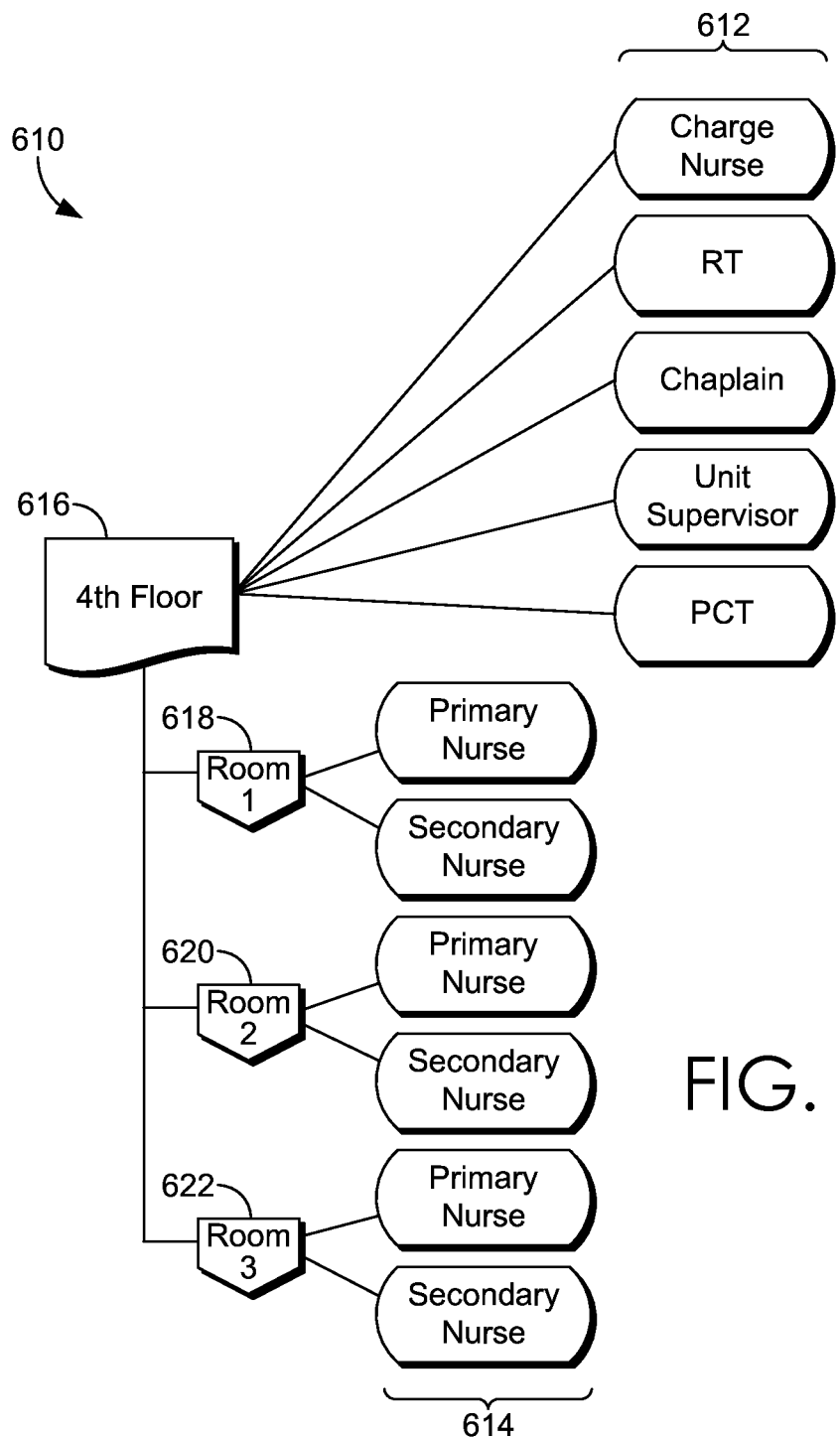
FIG. 6B is an exemplary chart illustrating various roles associated with a location.

FIGS. 6A-6C illustrate examples of various roles associated with entities. FIG. 6A depicts a chart 600 of various roles 602 associated with a particular hospital service 604. In this example, the various roles 602 associated with the hospital service 604 "Cardiology" include: On Call Resident, On Call Fellow, On Call Attending, Resident 1, Resident 2, Resident 3, Resident 4, Outside Calls Attending, Consult Fellow, Consult Attending, and Acting Intern.

FIG. 6B depicts a chart 610 of roles associated with a location. A first set of roles 612 is associated with the location 616 "4th Floor." The first set of roles 612 includes: Charge Nurse, RT, Chaplain, Unit Supervisor, and PCT. A second set of roles 614 is associated with particular rooms 618, 620, 622 within the location 616 of "4th Floor." Each of a first room 618, a second room 620, and a third room 622 are associated with its own Primary Nurse and Secondary Nurse.

FIG. 6C depicts two examples 630, 640 of roles associated with teams. In the first example 630, the roles of "Fellow" 632, "Resident" 634, and "Acting Intern" 636 are associated with "Medical Team" 638. In the second example 640, the roles of "Fellow" 642 and "Resident" 644 are associated with "Surg/Neuro Team" 646.

Returning to FIG. 2, the routing service 220 is in communication with the information manager 250 and an escalation service 222, a contact preferences data store 224, a presence detection component 226, and a proximity component 228. The routing service 220 functions to determine a path which a communication takes to reach a user associated with a particular role.

The escalation service 222 re-routes information to one or more backup users in the event that the user associated with the original role does not respond or rejects the communication. For example, when information is communicated that requires an action, the information may be communicated to a different, backup role when no response is received after a predetermined period of time. Alternatively, the communication could request a response and the user could respond by manually rejecting the communication. For example, the initial communication may have been communicated to a patient's assigned nurse. If the nurse does not respond within a predetermined time period associated with the alert, the alert may be communicated to a second individual based on role (e.g., a charge nurse of the floor at that particular time). In another example, the initial communication may have been sent to On-Call Resident 1. The user holding that role could manually reject the communication, and the communication would then be re-routed to On-Call Resident 2 automatically. The information may also be escalated to an individual that has manually claimed a role for a particular time. For example, a schedule may indicate Nurse X is the charge nurse at that time but, in reality, Nurse A is the current charge nurse (e.g., Nurse X and Nurse A switched shifts, Nurse X is running late, etc.). Manual role claiming may not always correspond with a scheduled role, as illustrated in the previous example. In embodiments, manual role claiming overrides automatic role assignments.

In embodiments, reminders may be associated with the escalation information. For instance, the initial nurse that received the information (in the above example) may have a reminder communicated to the nurse prior to the expiration of the predetermined time period for response. Once escalated, the subsequent recipient may also receive a reminder. The reminders may continue to be communicated to each recipient along the way until a required action is received.

The system may also automatically identify conflicts and, as a result, automatically re-route communications, reassign roles, and the like. For instance, if a clinician has something come up during the day that is put into the schedule, the system may identify the conflict and reassign the role automatically to a designated backup. As an additional example, an on-call surgeon may have an emergency surgery and not be able to respond to alerts. The system may recognize the on-call contact is currently in surgery and automatically re-route information to a backup user.

In embodiments, more than one backup may be utilized. For instance, a user may indicate that they are busy and critical messages are to be sent to Clinician 1, but non-critical or routine messages are to go to Clinician 2.

The contact preferences data store 224 of FIG. 2 stores contact preferences for all of the users in the healthcare system. A healthcare system may be just one clinic, or it could include a whole network of hospitals. Contact preferences specify a modality by which a user is to be contacted in particular circumstances. A clinician may, for example, indicate that alerts of one kind are to be delivered one way but alerts of another kind are to be delivered in a different way. For instance, non-critical information may be designated by a clinician to be delivered via email while critical information may be designed by a clinician to be delivered as a text message alert.

Figures 8, 9, 10:
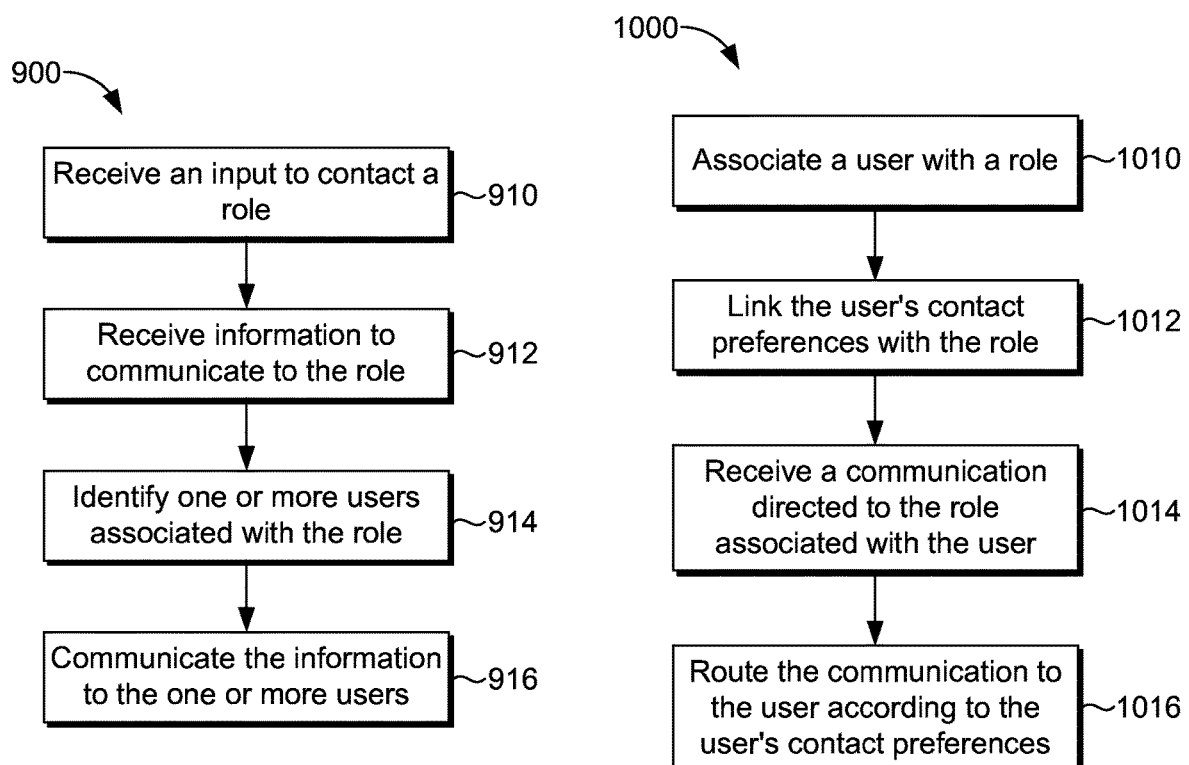
FIG. 8 depicts an exemplary chart of user contact preferences in accordance with an embodiment of the present invention.
FIG. 9 is a flow diagram that illustrates an exemplary method of routing information to a user based on the user's role.
FIG. 10 is a flow diagram that illustrates an exemplary method of routing a communication to a user based on the user's role.

FIG. 8 depicts an exemplary chart 800 of contact preferences for a given user. The chart includes information for "Urgency" 802, "Day" 804, "Time" 806, "Modality" 808, and "Address" 810. "Urgency" 802 describes whether a communication is critical or routine. For example, a "Stat" or "Critical" alert may require immediate attention of a clinician. Alternatively, a "Routine" or "Non-critical" communication may simply be a message which can be addressed at the clinician's discretion. The "Day" 804 and "Time" 806 simply set the parameters for when certain types of communications are to be directed to different modalities of communication. The "Modality" 808 refers to the method by which the communication reaches the user. The "Address" 810 specifies the e-mail address, phone number, fax number, etc. to which a communication is directed. In this example on the first line 812, all "Stat" communications received on Monday from 7 am to 7 pm are to be directed to the clinician's office phone number, which is 784.355.9802. In the second line 814, the chart shows that "Stat" communications received on Monday from 7 am to 10 pm can also be directed to the clinician's mobile phone number, which is 123.456.7890. According to the third line 816, all "Routine" communications sent on Monday from 7 am to 7 pm are to be directed to the email address doctor@client.org. The fourth line specifies that "Routine" communications on Monday from 7 am to 10 pm may also be directed to the email address personal@gmail.com. Additionally, the system may automatically associate modes of communication with specific information. For instance, the system may include rules that determine that some information is to be communicated in a certain way regardless of individual contact preferences.

Returning to FIG. 2, the presence detection component 226 determines whether a clinician is actually present. This information may be used to determine whether a user is associated with a given role. For instance, a clinician may be identified as scheduled to be associated with a role for a particular time period but the system may recognize whether or not the clinician is actually present (e.g., in the facility, logged into the system, etc.). Criteria defining what constitutes presence may be client-defined such that a facility can determine what is most appropriate for its circumstances.

The proximity component 228 routes information to users which are closest to a relevant location. Proximity may be used separately or in combination with role-based routing. Proximity-based routing, as used herein, refers generally to routing information to users that are closest to a relevant location. For instance, if a patient with a fall-risk has fallen, an alert that the patient has fallen may be routed to a nearest clinician that can help. Additionally, the proximity-based routing may be used in conjunction with role-based routing. For example, in the above illustration where a fall-risk patient has fallen, choosing a nearby clinician to help is certainly important but it should also be an appropriate clinician. For example, a nearby nurse is an appropriate clinician to contact whereas a nearby respiratory therapist may not be as appropriate. Thus, proximity-based rules may be used in combination with role-based rules. Proximity may be based on the location to which a user is assigned to work at a given time. Alternatively, a user's proximity to a given location may be determined electronically using GPS-enabled mobile devices, radio-frequency identification (RFID) tags, and the like.

The communication delivery service 230 is in communication with the information manager 250. The communication delivery service 230 functions to receive messages from users and alerts from machines to deliver to users in the healthcare system. The routing service 220 determines where and how communications are to be delivered and the communication delivery service 230 executes the deliveries.

The role association service 240 is in communication with the information manager 250 and comprises a personnel scheduler 242, an assignment manager 244, and a manual claiming service 246. The role association service 240 associates users with roles and groups based on schedules, assignments, and manual claiming. Once a user is associated with a role, any communication sent to the role will be routed to the user.

The personnel scheduler 242 automatically assigns users to roles in accordance with schedules. For example, Dr. Smith may be scheduled to be on-call Sunday evening. At 6 pm Sunday, the role of "On-call Radiologist" will be automatically be associated with Dr. Smith's contact information and contact preferences. The personnel scheduler 242 may also take into account location assignments. For instance, Nurse A and Nurse B may both be scheduled to work in the same role at the same time. However, Nurse A is assigned to rooms 1 and 2 while Nurse B is assigned to rooms 3 and 4. The system will automatically update so that communications relevant to rooms 1 and 2 are routed to Nurse A while communications relevant to rooms 3 and 4 are routed to Nurse B.

The manual claiming service 246 enables a user to manually claim a role which that user wants to be associated with. For example, Dr. X may not be scheduled to work on Wednesday, but is called in to cover for Dr. Y. Upon arriving at the hospital, Dr. X may manually claim the role of Attending Physician, overriding the schedule. Then, all communications directed to Attending Physician would be routed to Dr. X instead of Dr. Y.

The assignment manager 244 associates roles with users based on manual inputs from other users. For example, User A may be in charge of scheduling nursing shifts. User B was originally scheduled to be the Primary Nurse for Room 1 on Friday. User B called in sick. User A called User C to cover the shift and when User C arrives at the hospital, User A manually assigns the role of Primary Nurse for Room 1 to User C. The manual assignment made by User A overrides the existing schedule.

FIGS. 7A and 7B depict an exemplary graphical user interface (GUI) 700 for a user to claim a role. In FIG. 7A, the GUI displays the name of the role 702, "On-call Cardiologist," and indicates that the role is "Unclaimed" at the status indicator 704. The contact information area 706 indicates the method by which a user holding this role may be contacted. Here, for example, the on-call cardiologist could be contacted by dialing extension 4444. There is a 'favorites' button 708 to add the role to a user's list of favorites. There may also be a user photo area 710, which remains empty when the role is unclaimed. FIG. 7B depicts the same GUI 700 after a user has claimed the role of on-call cardiologist. Here, the user name 712 of the user claiming the role is "Rita Vanderveen." The status indicator 704 now indicates that the user associated with the role is "Available" and there is a user photo displayed in the user photo area 710. Now, when another user dials extension 4444, Rita Vanderveen will be contacted.

It should be understood that this and other arrangements described herein are set forth only as examples. Other arrangements and elements (e.g., machines, interfaces, functions, orders, and groupings of functions, etc.) can be used in addition to or instead of those described, and some elements may be omitted altogether. Further, many of the elements described herein are functional entities that may be implemented as discrete or distributed components or in conjunction with other components/modules, and in any suitable combination and location. Various functions described herein as being performed by one or more entities may be carried out by hardware, firmware, and/or software. For instance, various functions may be carried out by a processor executing instructions stored in memory.

The content and volume of such information in the data stores described herein are not intended to limit the scope of embodiments of the present invention in any way. Further, though described as single, independent components, the data stores may, in fact, be a plurality of storage devices, for instance, a database cluster, portions of which may reside on the routing service and/or the end-user computing device.

FIG. 9 depicts a flow diagram of an exemplary method 900 of communicating information to a user based on the user's role. At a step 910, an input is received to contact a particular role. The input may be received by a communication delivery service such as the communication delivery service 230 of FIG. 2. The role is a position held by a set of users satisfying one or more criteria. The set of users may be one user or a plurality of users. The criteria may be defined by one or more of a job title, a hospital, service, a location, and the like. The input may come from another user, a computing system, or a medical device.

At a step 912, information to communicate to the role is received. The information may be received by a communication delivery service such as the communication delivery service 230 of FIG. 2. The information may include one or more of a patient status, an emergency alert, a medical device alert, a patient alert, a coding situation, a test result, or a general message. The information may be urgent or routine.

At a step 914, one or more users associated with the particular role are identified. The identification may be performed by a routing service such as routing service 220 of FIG. 2. The identification process may rely on information from a directory and/or a role association service, such as directory 210 and role association service 240. An individual user of the set of users may be associated with the role in different ways. The individual could manually claim the role, utilizing a manual claiming service such as the manual claiming service 246 of FIG. 2. The individual could be automatically assigned the role according to a schedule according to a personnel scheduler, such as the personnel scheduler 242 of FIG. 2. Alternatively, the individual may be manually assigned the role by another user utilizing an assignment manager, such as assignment manager 244 of FIG. 2. The role may be associated with a plurality of individuals as part of a location group, a specialty group, or a team.

Finally, at a step 916, the information is communicated to the one or more users associated with the role. The information may be communicated by a communication delivery service, such as communication delivery service 230 of FIG. 2. The communication delivery service 230 may rely on routing information from a routing service 220 and contact information from a directory 210.

After delivering the information to the one or more users associated with the role, the system may receive a rejection of the communicated information. The rejection may be received by a communication delivery service, such as communication delivery service 230 of FIG. 2. The rejection may come in the form of a manual rejection received from the set of users or the rejection may be a lack of response from the set of users which is registered automatically after a given period of time. The information is then re-routed to a set of backup users associated with a backup role. The information may be re-routed using an escalation service, such as the escalation service 222 of FIG. 2. The backup role may be associated with one or more users by manually claiming the backup role, being automatically assigned to the backup role according to a schedule, or being manually assigned to the backup role by another user.

For example, a patient alert is sent to Nurse A requesting assistance to help a patient to the bathroom. However, User A is otherwise occupied by assisting Doctor X with a patient examination in another room. User A could respond to the request with a rejection, immediately notifying the system to re-route the information to a backup user. Alternatively, Nurse A may not respond to the request at all, in which case the system will automatically register a rejection after a minute has passed without response. After the system has registered a rejection, either manually or automatically, the patient alert is re-routed to Nurse A's backup, Nurse B. Nurse B responds to the request, accepting the task. The notifications cease and Nurse B attends to the patient.

FIG. 10 depicts a flow diagram of an exemplary method 1000 of routing communications to a user based on the user's role. At a step 1010, a user is associated with a role. The role is a position held by one or more users satisfying one or more criteria, wherein the one or more criteria are defined by one or more of a job title, a hospital service, or a location. As described above, a user may be associated with a role by manually claiming the role, being automatically assigned to the role according to a schedule, or being manually assigned to the role by another user. The user may be associated with a role by utilizing a role association service, such as role association service 240 of FIG. 2. One user may have multiple roles on any given day or different roles on different days. A user may be associated with more than one role at one time, and therefore multiple extensions or modes of communication associated with the multiple roles will route information to that user. For instance, if Dr. Brown is the on-call cardiologist but also the head of cardiology, communications directed to both of those roles will contact Dr. Brown.

At a step 1012, the user's contact preferences are linked with the role. This may be accomplished by utilizing a contact preferences data store, such as the contact preferences data store 224 in association with the routing service 220 of FIG. 2. Contact preferences specify a modality of contacting the user for a given date, time and/or urgency of the communication. An example of a user's contact preferences are shown in the chart of FIG. 8.

At a step 1014, a communication directed to the role associated with the user is received. The communication may be received by a communication delivery service, such as the communication delivery service 230 of FIG. 2. The communication may be a phone a call, an email, a text message, an SMS message, a medical device alarm, or other alert.

Finally, at a step 1016, the communication is routed to the user according to the user's contact preferences. This may be accomplished by utilizing a communication delivery service working in conjunction with the information from a routing service, such as the communication delivery service 230 and routing service 220 of FIG. 2. The communication may also be routed to a user based on the user's proximity to a particular location. The user's proximity may be used to route a communication to a user according to a proximity component, such as proximity component 228 in communication with the routing service 220 of FIG. 2. Alternatively, the user's presence may be taken into account when routing a communication to a role. A user's presence may be detected with a presence detection component, such as presence detection component 226 of FIG. 2. For example, a clinician may be identified as scheduled to be associated with a role for a particular time period but the system may recognize whether or not the clinician is actually present (e.g., in the facility, logged into the system, etc.).

After the communication is routed to the user, the system may request a response from the user. An escalation service, such as escalation service 222, may determine whether to re-route a communication to a backup user based on whether the original user responds. If the user responds to the request, the communication is delivered to the user by a communication delivery service, such as communication delivery service 230 of FIG. 2. Alternatively, if the user fails to send a response, the communication may be re-routed to a backup role. The backup role may be determined based on a schedule, manual assignment, or manual claiming of a backup role.

Scheduling information may also include breaks for clinicians such that when a clinician in a claimed role is on break, the system automatically removes them from the role since they may not be responding and associates the role with a back-up contact for that role for the particular period of time. Alternatively, the system may communicate to the on-break clinician associated with the role and a back-up clinician covering while the originally assigned clinician is on break.

Additional embodiments are directed to intelligent routing of information involving remote information. For example, a patient may have a chronic condition and manage the condition remotely. In that situation, roles may still be claimed for the remote patient. For instance, an on-call clinician may still claim the role of on-call clinician for that patient in the case of an emergency. Calls received from the patient could be routed to the appropriate role based on the needs of the patient.

Remote devices may also be included in the present invention. For example, numerous medical devices may be programmed to notify of alerts. The alerts from the devices may be integrated into the system of the present invention such that notifications may be communicated via role-based or role-based and proximity-based routing. Additionally, users may have the ability to respond or take action on the device through the role-based routing system. For example, an alert from a medical device may be communicated, via role-based (or role-based and proximity-based) routing. The recipient may then respond to the alert via the role-based system and take actions including turning off the alarm on the device itself, holding the alarm on the device itself, holding the alarm for a predetermined period of time before it sounds again or is rerouted, and the like. This is beneficial since some times the alerts are self-resolving. For example, $O_2$ alerts are oftentimes self-resolving so the ability to hold the alarm remotely is helpful since it may resolve and no further alarm will be sounded. This improves efficiency and workflows of the users.

Additional embodiments of the present invention provide a multi-facility feature. This includes the ability to communicate with a healthcare system that spans multiple locations. For example, a hospital may have more than one campus. Each campus may be included in the system. As such, a unified directory may be used system wide. In that aspect, information may be routed across each location, thus improving communication efficiency.

The present invention has been described in relation to particular embodiments, which are intended in all respects to be illustrative rather than restrictive. Further, the present invention is not limited to these embodiments, but variations and modifications may be made without departing from the scope of the present invention.

The invention claimed is:

1. One or more non-transitory computer-storage media having computer-executable instructions embodied thereon that, when executed, perform a method of communicating information to a user based on the user's role, the method comprising:
   receiving an input to contact a first role, wherein the first role is a position that is associated with a location;
   receiving information to communicate to the first role, wherein the first role is associated with a role-specific mode of communication;
   determining a location of one or more users based on a location of at least one tracked item of the one or more users;
   based on the location of the one or more users and the location associated with the first role, associating, without user input, the one or more users with the first role;
   in response to associating the one or more users with the first role, determining one or more user-specific modes of communication for communicating the information received to the one or more users associated with the first role;
   routing, without user input, the communication to the one or more users associated with the first role according to the one or more user-specific modes of communication;
   receiving an indication from the one or more users associated with the first role indicating whether the one or more users associated with the first role accepted or rejected the information communicated;
   determining a location of one or more backup users based on the location of one or more tracked items of the one or more backup users; and
   based on the determined location of the one or more backup users, electronically redirecting the information to the one or more backup users, without user input, when the information communicated was rejected by or no response is received from at least one of the one or more users associated with the first role.

2. The media of claim 1, wherein the first role is associated with one or more criteria defined by one or more of a job title, a hospital service, or a location.

3. The media of claim 1, wherein the first role is associated with a plurality of individuals as part of a location group, a specialty group, or a team.

4. The media of claim 1, wherein an individual user of the one or more users is associated with the first role when one or more of: the individual user manually claims the role, the individual user is automatically assigned the role according to a schedule, or the individual user is manually assigned the role by another user.

5. The media of claim 1, wherein the information includes one or more of:
   a patient status;
   an emergency alert;
   a medical device alert;
   a patient alert;
   a coding situation;
   a test result; or
   a general message.

6. The media of claim 1, further comprising receiving a rejection of the communicated information from the one or more users, and electronically re-routing the information to the one or more backup users that are associated with a backup role that is different from the first role.

7. The media of claim 6, wherein the backup role is associated with an individual backup user of the one or more backup users when one or more of: the individual backup user manually claims the backup role, the individual backup user is automatically assigned the backup role according to a schedule, or the individual backup user is manually assigned the backup role by another user.

8. The media of claim 6, wherein the rejection is a manual rejection received from the one or more users.

9. The media of claim 6, wherein the rejection is a lack of response from the one or more users which are registered automatically after a given period of time.

10. A computerized method carried out by at least one server having at least one processor for routing communications to a user based on the user's role, the method comprising:
   determining a location of one or more users based on a location of at least one tracked item of the one or more users;
   based on the location of the one or more users and a location associated with a first role associating, without user input, a first user with the first role, wherein the first role is associated with a location;

linking a first user's contact preferences with the first role;

receiving a communication directed to the first role associated with the first user, wherein the first role is associated with a role-specific mode of communication;

in response to receiving the communication, determining a user-specific mode of communication that corresponds to the first user's contact preference that are linked to the first role;

routing, without user input, the communication to the first user according to the determined user-specific mode of communication;

receiving an indication from the first user indicating whether the first user accepted or rejected the information communicated;

determining a location of one or more backup users based on a location of one or more devices of the one or more backup users; and based on the determined location of the one or more backup users, electronically redirecting the information to the one or more backup users, without user input, when the information communicated was rejected by or no response is received from the first user associated with the first role.

11. The method of claim 10, wherein the first user is associated with the first role when one or more of: the first user manually claims the first role, the first user is automatically assigned the first role according to a schedule, or the first user is manually assigned the first role by another user.

12. The method of claim 10, wherein the communication is a phone call, e-mail, text message, SMS message, medical device alarm, or other alert.

13. The method of claim 10, wherein the communication is directed to the first role based on the first user's proximity to a particular location.

14. The method of claim 10, wherein the user's contact preferences specify a modality of contacting the user for one or more of a given date, time, or urgency of the communication.

15. The method of claim 10, further comprising requesting a response from the first user, and upon receiving a response, delivering the communication to the first user.

16. The method of claim 10, further comprising requesting a response from the first user, and upon failure to receive a response, automatically re-routing the communication to a backup role.

17. A computer-implemented system for communicating information to an user based on their role, the computer-implemented system comprising:

a directory comprising a data store of user names for users, contact information, and one or more roles;

a communication service for determining a role-specific mode of communication through which information is to be communicated to each of the one or more roles;

a routing service for determining, without user input, one or more user-specific modes of communication used to communicate with the users;

a communication delivery service for electronically sending communications of the information to the users;

a proximity component for determining a location of the users and one or more backup users based on a location of at least one tracked item;

a role association service for associating, without user input, the users with a first role, based on the location of the users, and a location associated with the first role; and an escalation service for electronically rerouting the information to one or more backup users, without user input, based on the determined location of the one or more backup users, when at least one of the users associated with the first role does not respond to or rejects the communications of the information.

18. The system of claim 17, wherein the directory further comprises a role-defining service that links the user names and contact information with the roles.

19. The system of claim 17, wherein the routing service comprises:

an escalation service for forwarding messages;

a contact preferences data store;

a presence detection component; and a proximity component.

20. The system of claim 17, wherein the role association service comprises:

a personnel scheduler, an assignment manager, and a manual claiming service.

* * * * *